United States Patent [19]
Prakash et al.

[11] Patent Number: 6,146,680
[45] Date of Patent: Nov. 14, 2000

[54] METAL COMPLEXES OF N-[N-(3,3-DIMETHYLBUTYL)-L-α-ASPARTYL]-L-PHENYLALANINE 1-METHYL ESTER

[75] Inventors: Indra Prakash, Hoffman Estates; Zhi Guo, Chicago, both of Ill.

[73] Assignee: The NutraSweet Company, Chicago, Ill.

[21] Appl. No.: 09/146,965

[22] Filed: Sep. 4, 1998

Related U.S. Application Data

[60] Provisional application No. 60/058,508, Sep. 11, 1997.

[51] Int. Cl.[7] ................................... A23L 1/236
[52] U.S. Cl. ........................ 426/548; 560/40; 560/41
[58] Field of Search .................. 426/548; 560/40, 560/41

[56] References Cited

U.S. PATENT DOCUMENTS

| | | | |
|---|---|---|---|
| 4,031,258 | 6/1977 | Haas | 426/548 |
| 4,153,737 | 5/1979 | Berg | 426/548 |
| 4,448,716 | 5/1984 | Tsau | 260/112.5 |
| 5,480,668 | 1/1996 | Nofre | 426/548 |
| 5,510,508 | 4/1996 | Claude | 560/41 |
| 5,728,862 | 3/1998 | Prakash | 560/40 |

OTHER PUBLICATIONS

T.P. Labuza et al., "The Kinetics of Nonenzymatic Browning", Physical Chemistry of Foods, Chapter 14, pp. 595–649, Marcel Dekker, Inc., New York (1992).

E. Benedetti et al., "The Structure of New Peptide Tast Ligands", Structure, Folding, and Conformational Analysis, P233, Amer. Peptide Symp., Nashville, Tennessee (1997).

*Primary Examiner*—Leslie Wong
*Attorney, Agent, or Firm*—Fitzpatrick, Cella, Harper & Scinto

[57] ABSTRACT

Dipeptide sweeteners are disclosed that are metal complexes of N-[N-(3,3-dimethylbutyl)-L-α-aspartyl]-L-phenylalanine 1-methyl ester represented by the formula

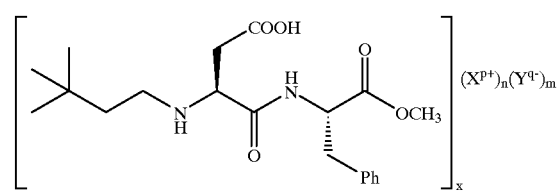

wherein $X^{p+}$ is selected from the group consisting of $Al^{3+}$, $Fe^{2+}$, $Fe^{3+}$, $Ca^{2+}$, $Mg^{2+}$ and $Zn^{2+}$; $Y^{q-}$ is selected from the group consisting of $Cl^-$, $SO_4^{2-}$, $PO_4^{3-}$ and $CH_3COO^-$; x is a number from 1 to 4 and pn=qm. Also disclosed is a liquid low-calorie sweetener containing such metal complexes.

5 Claims, 1 Drawing Sheet

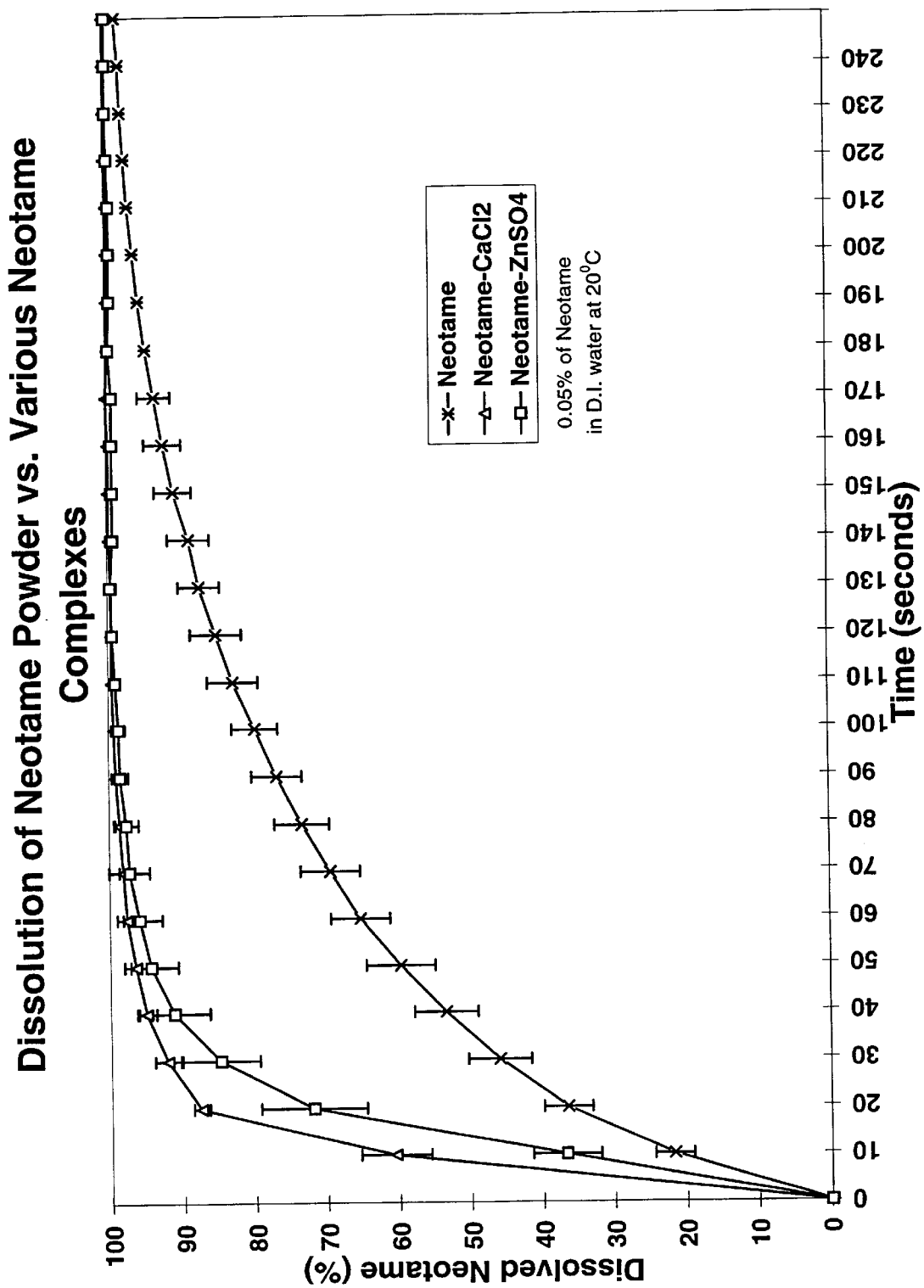

METAL COMPLEXES OF N-[N-(3,3-DIMETHYLBUTYL)-L-α-ASPARTYL]-L-PHENYLALANINE 1-METHYL ESTER

This invention claims the benefit of U.S. Provisional Application Ser. No. 60/058,508, filed Sep. 11, 1997.

BACKGROUND OF THE INVENTION

1. Field of the Invention

This invention relates to novel sweeteners. In particular, the invention relates to metal complexes of the N-alkylated aspartame derivative, N-[N-(3,3-dimethylbutyl)-L-α-aspartyl]-L-phenylalanine 1-methyl ester, i.e., neotame. The invention also relates to a liquid low calorie sweetener containing such metal complexes.

2. Related Background Art

It is known that various N-substituted derivatives of aspartame, such as disclosed in U.S. Pat. No. 5,480,668, are useful as sweetening agents. In particular, the N-alkylated aspartame derivative, N-[N-(3,3-dimethylbutyl)-L-α-aspartyl]-L-phenylalanine 1-methyl ester, is known as an extremely potent sweetening agent since its sweetening potency, on a weight basis, has been reported to be at least 50 times that of aspartame and about 10,000 times that of sucrose.

Since sweetening agents are often employed in aqueous solutions and beverages, it is important that they have an acceptable dissolution rate and an effective level of solubility to be commercially practicable. U.S. Pat. No. 4,031,258 describes certain inorganic salts of dipeptide sweeteners that provide improved dissolution and solubility. U.S. Pat. No. 4,448,716 describes dipeptide sweetener-metal complexes with improved dissolution rates, solubility and stability. N-[N-(3,3-dimethylbutyl)-L-α-aspartyl]-L-phenylalanine 1-methyl ester, however, is not disclosed or suggested.

It is known that the physical properties, as well as the stability of aspartame and other peptides can be modified by conversion to their salts. This is disclosed, for example, in U.S. Pat. Nos. 4,031,258 and 4,153,737. U.S. Pat. No. 4,153,737 also describes concentrated liquid low calorie sweeteners.

Structurally, however, N-[N-(3,3-dimethylbutyl)-L-α-aspartyl]-L-phenylalanine 1-methyl ester and aspartame differ in that, in N-[N-(3,3-dimethylbutyl)-L-α-aspartyl]-L-phenylalanine 1-methyl ester, a bulky neohexyl substituent is present on the amine nitrogen.

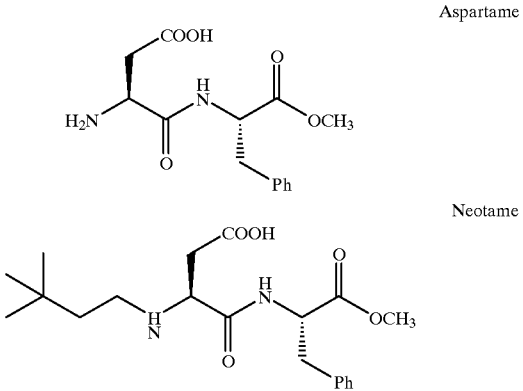

This structural difference results in dramatic differences in the physical and chemical properties of these compounds. For example, the melting point of N-[N-(3,3-dimethylbutyl)-L-α-aspartyl]-L-phenylalanine 1-methyl ester is 80° C., while that of aspartame is 248° C. In addition, N-[N-(3,3-dimethylbutyl)-L-α-aspartyl]-L-phenylalanine 1-methyl ester has much higher solubility in organic solvents than aspartame, and a much lower solubility in water. It is also known that N-[N-(3,3-dimethylbutyl)-L-α-aspartyl]-L-phenylalanine 1-methyl ester has a higher stability than aspartame under some pH conditions, as described in U.S. Pat. No. 5,480,688. The pronounced difference in sweetness between the two compounds is further evidence of their chemical dissimilarity.

Moreover, it is also known that a primary amino group such as the one on aspartame (pKa 7.7) generally has a different pKa than a secondary amino group such as the one on N-[N-(3,3-dimethylbutyl)-L-α-aspartyl]-L-phenylalanine 1-methyl ester (pKa 8.1). Moreover, the pKa's of an amino acid are known to have a profound impact on food applications (Labuza, T. P. and Basisier, M. W., 1992, "Physical Chemistry of Foods", H. G. Schwartzber and R. W. Hartel (Eds.), Marcel Dekker, Inc., New York). It is also well known that a secondary amine can not form Schiff base type compounds with carbonyl compounds while a primary amine may. Furthermore, N-[N-(3,3-dimethylbutyl)-L-α-aspartyl] -L-phenylalanine 1-methyl ester exhibits physiologically different behavior than aspartame as exemplified by the dramatic difference in sweetness. These differences are clearly indicative that the characteristics and properties of one can not be said to suggest those of the other.

While N-[N-(3,3-dimethylbutyl)-L-α-aspartyl]-L-phenylalanine 1-methyl ester is a highly potent sweetener, it is sparingly soluble in water and can give rise to dusting problems. Therefore, there is a need for N-[N-(3,3-dimethylbutyl)-L-α-aspartyl]-L-phenylalanine 1-methyl ester derivatives that have good dissolution and solubility properties in aqueous systems, and avoid dusting problems often encountered with fine powders. It would also be advantageous if the stability of N-[N-(3,3-dimethylbutyl)-L-α-aspartyl]-L-phenylalanine 1-methyl ester could be improved.

SUMMARY OF THE INVENTION

This invention relates to dipeptide sweeteners that are metal complexes of N-[N-(3,3-dimethylbutyl)-L-α-aspartyl]-L-phenylalanine 1-methyl ester possessing good dissolution and solubility properties in aqueous systems. In particular, the metal complexes of N-[N-(3,3-dimethylbutyl)-L-α-aspartyl]-L-phenylalanine 1-methyl ester of this invention are represented by the formula.

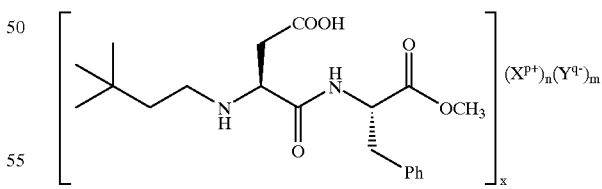

wherein $X^{p+}$ is selected from the group consisting of $Al^{3+}$, $Fe^{2+}$, $Fe^{3+}$, $Ca^{2+}$, $Mg^{2+}$ and $Zn^{2+}$; $Y^{q-}$ is selected from the group consisting of $Cl^-$, $SO_4^{2-}$, $PO_4^{3-}$, $HCOO^-$ and $CH_3COO^-$; x is a number from 1 to 4 and pn=qm. The invention is also related to a liquid low calorie sweetener containing the metal complexes of this invention.

BRIEF DESCRIPTION OF THE DRAWING

The FIGURE is a graph comparing the aqueous dissolution of N-[N-(3,3-dimethylbutyl)-L-α-aspartyl]-L- phenylalanine 1-methyl ester at a target concentration of 0.05% by weight with an equivalent neotame concentration, i.e., the concentration of the neotame in each case is the same, of the calcium chloride and zinc sulfate complexes of N-[N-(3,3-dimethylbutyl)-L-α-aspartyl]-L-phenylalanine 1-methyl ester.

DETAILED DESCRIPTION OF THE INVENTION

This invention is directed to metal complexes of N-[N-(3,3-dimethylbutyl)-L-α-aspartyl]-L-phenylalanine 1-methyl ester, i.e., metal complexes of neotame. U.S. Pat. No. 5,480,668, U.S. Pat. No. 5,510,508 and U.S. Pat. No. 5,728,862, which describe the preparation of N-[N-(3,3-dimethylbutyl)-L-α-aspartyl]-L-phenylalanine 1-methyl ester are incorporated by reference herein as if fully set forth. Thus, the starting material may be readily prepared by one of ordinary skill in the art without undue experimentation.

The metal complexes of this invention may be prepared by adding N-[N-(3,3-dimethylbutyl)-L-α-aspartyl]-L-phenylalanine 1-methyl ester and a metal salt to an amount of a solvent effective to dissolve both the N-[N-(3,3-dimethylbutyl)-L-α-aspartyl]-L-phenylalanine 1-ethyl ester and the metal salt, and then stirring for period of time to achieve formation of the metal complex. Suitable solvents include, water, methanol, ethanol, isopropanol, butanol, acetone, acetonitrile, tetrahydrofuran, dimethylformamide and dimethyl sulfoxide. The metal complex product may be recovered by evaporating the solvent in vacua. The metal complex product may also be recovered by freeze drying or spray drying the resulting solution.

The metal salts suitable for use in preparing the metal complexes of this invention include any of the salts formed between a metal cation, $X^{p+}$, selected from the group consisting of $Al^{3+}$, $Fe^{2+}$, $Fe^{3+}$, $Ca^{2+}$, $Mg^{2+}$ and $Zn^{2+}$; and an anion, $Y^{q-}$ selected from the group consisting of $Cl^-$, $SO_4^{2-}$, $PO_4^{3-}$ and $CH_3COO^-$. These salts will have the formula $(X^{p+})_n(Y^{q-})_m$, wherein pn=qm, so as to render the salt electrically neutral. The complexes of this invention need not have a N-[N-(3,3-dimethylbutyl)-L-α-aspartyl]-L-phenylalanine 1-methyl ester to salt ratio of 1:1, but also include variations thereof.

Particularly preferred metal complexes of this invention include those formed between calcium chloride, magnesium chloride, ferric chloride, aluminum chloride or zinc sulfate, and N-[N-(3,3-dimethylbutyl)-1-L-α-aspartyl]-L-phenylalanine 1-methyl ester.

The metal complexes of this invention provide a number of improved properties over those of N-[N-(3,3-dimethylbutyl)-L-α-aspartyl]-L-phenylalanine 1-methyl ester. In particular, the aqueous solubility is increased and the dissolution rate of the composition is greatly improved. These neotame metal complexes are sweet in taste. It is also believed that these sweetener metal complexes will have improved stability. Thus, the metal complexes of N-[N-(3, 3-dimethylbutyl)-L-α-aspartyl]-L-phenylalanine 1-methyl ester will be particularly useful in beverage systems, particularly since additional methods or mechanical preparations are diminished or not necessary to provide for quick dissolution such as desired in a table top sweetener. The metal complexes of this invention may be admixed with known bulking agents to prepare tablets, powdered and granular sweeteners using methods well known to those skilled in the art. Another advantage of the metal complexes of this invention is that they do not exhibit the dusting problems associated with N-[N-(3,3-dimethylbutyl)-L-α-aspartyl]-L-phenylalanine 1-methyl ester.

The metal complexes may also be used to prepare a liquid, low-calorie sweetener by dissolving a high concentration of the metal complex of this invention in an aqueous or alcoholic system, e.g., water, propylene glycol, water/propylene glycol, ethanol or a water/ethanol mixture. Such a liquid, low-calorie sweetener may find utility in such foodstuffs as gelatin desserts, fruit flavored beverages, cereal, cake mixes, fruit juices, syrups, salad dressings, pet foods, carbonated soft drinks, table top sweeteners and the like. Such utilities are not restrictive since other applications may include cough medicines, tonics and the like. One embodiment of this invention of particular interest contemplates a liquid table top sweetener as a replacement for sucrose and other known sweeteners. The liquid low calorie sweetener generally will contain up to about 40% by weight of the metal complex of N-[N-(3,3-dimethylbutyl)-L-α-aspartyl]-L-phenylalanine 1-methyl ester, the concentration depending, of course, on the desired end use.

The Examples which follow are intended as an illustration of certain preferred embodiments of the invention, and no limitation of the invention is implied.

EXAMPLE 1

Calcium Chloride Complex of N-[N-(3,3-dimethylbutyl)-L-α-aspartyl]-L-phenylalanine 1-methyl ester Calcium chloride dihydrate (3.23 g, 0.0220 mol) and N-[N-(3,3-dimethylbutyl)-L-α-aspartyl]-L-phenylalanine 1-methyl ester N-[N-(3,3-dimethylbutyl)-L-α-aspartyl]-L-phenylalanine 1-methyl ester (8.72 g, 0.0220 mol) were dissolved in 80 ml of methanol. The bulk of the methanol was removed from the resulting clear solution using a rotary evaporator at 33° C. under house vacuum. The residual solvent was removed using a mechanical vacuum pump, yielding the title complex (11.2 g). This complex (0.2 g) dissolved in water (100 mL) in less than 120 seconds (visual observation) and 140 seconds (spectrophotometric determination).

EXAMPLE 2

Magnesium Chloride Complex of N-[N-(3,3-dimethylbutyl)-L-α-aspartyl]-L-phenylalanine 1-methyl ester Magnesium chloride hexahydrate (6.80 g, 0.0334 mol) and N-[N-(3,3-dimethylbutyl)-L-α-aspartyl]-L-phenylalanine 1-methyl ester (13.26 g, 0.0334 mol) were dissolved in 100 mL of methanol. The bulk of the methanol was removed from the resulting clear solution using a rotary evaporator at 33° C. under house vacuum. The residual solvent was removed using a mechanical vacuum pump, yielding the title complex (17.7 g). This complex (0.2 g) dissolved in water (100 mL) in less than 120 seconds (visual observation).

EXAMPLE 3

Zinc Sulfate Complex of N-[N-(3,3-dimethylbutyl)-L-α-aspartyl]-L-phenylalanine 1-methyl ester Zinc sulfate heptahydrate (8.86 g, 0.0308 mol) and N-[N-(3,3-dimethylbutyl)-L-α-aspartyl]-L-phenylalanine 1-methyl ester (12.21 g, 0.0308 mol) were dissolved in 120 ml of methanol. The bulk of the methanol was removed from the resulting clear solution using a rotary evaporator at 33° C. under house vacuum. The residual solvent was removed using a mechanical vacuum pump, yielding the title complex (17.2 g). This complex (0.2 g) dissolved in water (100 mL) in less than 140 seconds (visual observation) and 180 seconds (spectrophotometric determination).

COMPARATIVE EXAMPLE 1

Dissolution of N-[N-(3,3-dimethylbutyl)-L-α-aspartyl]-L-phenylalanine 1-methyl ester in Water N-[N-(3,3-dimethylbutyl)-L-α-aspartyl]-L-phenylalanine 1-methyl ester (0.1–0.2 g) was dissolved in water (100 mL). The compound completely dissolved in 5–8 minutes (visual observation). The dissolution of 1.0 g of N-[N-(3,3-dimethylbutyl)-L-α-aspartyl]-L-phenylalanine 1-methyl ester in 100 mL of water required approximately 45 minutes.

Other variations and modifications of this invention will be obvious to those skilled in this art. This invention is not to be limited except as set forth in the following claims.

What is claimed is:

1. A metal complex of N-[N-(3,3-dimethylbutyl)-L-α-aspartyl]-L-phenylalanine 1-methyl ester represented by the formula

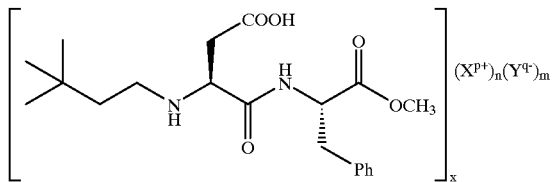

wherein $X^{p+}$ is selected from the group consisting of $Al^{3+}$, $Fe^{2+}$, $Fe^{3+}$, $Ca^{2+}$, $Mg^{2+}$ and $Zn^{2+}$; $Y^{q-}$ is selected from the group consisting of $Cl^-$, $SO_4^{2-}$, $PO_4^{3-}$ and $CH_3COO^-$; x is a number from 1 to 4 and pn=qm.

2. A metal complex according to claim 1, wherein $(X^{p+})_n(Y^{q-})_m$ is calcium chloride, magnesium chloride, ferric chloride, aluminum chloride or zinc sulfate.

3. A liquid low-calorie sweetener composition comprising a metal complex of a dipeptide-sweetener represented by the formula

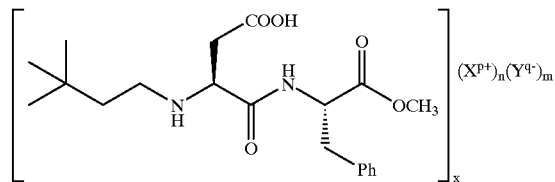

wherein $X^{p+}$ is selected from the group consisting of $Al^{3+}$, $Fe^{2+}$, $Fe^{3+}$, $Ca^{2+}$, $Mg^{2+}$ and $Zn^{2+}$; $Y^{q-}$ is selected from the group consisting of $Cl^-$, $SO_4^{2-}$, $PO_4^{3-}$ and $CH_3COO^-$; x is a number from 1 to 4 and pn=qm, dissolved in a consumable solvent or solvents in a concentration up to about 40% by weight of the composition to provide a high concentration liquid low-calorie sweetener.

4. A liquid low-calorie sweetener according to claim 3, wherein the solvent is ethanol, propylene glycol, water, ethanol/water or propylene glycol/water.

5. A liquid low-calorie sweetener according to claim 4, wherein $(X^{p+})_n(Y^{q-})_m$ is calcium chloride, ferric chloride, aluminum chloride, magnesium chloride or zinc sulfate.

* * * * *

UNITED STATES PATENT AND TRADEMARK OFFICE
CERTIFICATE OF CORRECTION

PATENT NO.   : 6,146,680
DATED        : November 14, 2000
INVENTOR(S)  : Indra Prakash et al.

Page 1 of 1

It is certified that error appears in the above-identified patent and that said Letters Patent is hereby corrected as shown below:

<u>Title page, item [56],</u>
References Cited, Other Publications, after "E. Benedetti et al.", "Tast" should read -- Taste --.

<u>Column 3,</u>
Line 30, "in vacua." should read -- in vacuo. --;
Line 37, "$Y^{q-}$" should read -- $Y^{q-}$, --.

<u>Column 6,</u>
Line 3, "Cl_," should read -- Cl$^-$, --.

Signed and Sealed this

Sixteenth Day of October, 2001

*Attest:*

NICHOLAS P. GODICI
*Attesting Officer*   Acting Director of the United States Patent and Trademark Office